United States Patent [19]
Goyal

[11] Patent Number: 5,991,660
[45] Date of Patent: Nov. 23, 1999

[54] CARDIAC PACING METHODS

[75] Inventor: Rajiva Goyal, Ann Arbor, Mich.

[73] Assignee: The Regents of the University of Michigan, Ann Arbor, Mich.

[21] Appl. No.: 09/094,199

[22] Filed: Jun. 9, 1998

Related U.S. Application Data

[63] Continuation-in-part of application No. 08/932,785, Sep. 18, 1997, Pat. No. 5,836,985.

[51] Int. Cl.$^6$ .................................................. A61N 1/362
[52] U.S. Cl. ............................................................ 607/14
[58] Field of Search .................................. 607/14, 3, 9, 5

[56] References Cited

U.S. PATENT DOCUMENTS

| | | | |
|---|---|---|---|
| 5,458,622 | 10/1995 | Alt | 607/15 |
| 5,509,925 | 4/1996 | Adams et al. | 607/15 |
| 5,549,661 | 8/1996 | Kordis et al. | 607/99 |

Primary Examiner—Scott M. Getzow
Attorney, Agent, or Firm—Medlen & Carroll, LLP

[57] ABSTRACT

The described method of treatment relates to the field of cardiovascular disease and is a cure for various forms of heart fibrillation. The method consists of sectioning the heart into independent conduction zones such that electrical communication between the zones is terminated. The communication between the zones is then reestablished in such a manner as to restore normal heart rhythm, by way of a pacing mechanism, thereby eliminating the fibrillation.

15 Claims, 8 Drawing Sheets

CARDIAC PACING METHODS

The present application is a continuation-in-part of U.S. Pat. Ser. No. 08/932,785, U.S. Pat. No. 5,836,985 filed Sep. 18, 1997.

FIELD OF INVENTION

The present invention relates to the field of cardiovascular disease and more particularly, the treatment of fibrillation including but not limited to atrial fibrillation.

BACKGROUND

Atrial fibrillation (AF) involves rapid and chaotic beating of the individual fibers of the heart muscle such that synchronous contraction is not maintained. This inevitably results in that part of the heart ceasing to pump blood, which in turn can lead to embolic stroke. Atrial fibrillation is characterized by the presence of multiple reentrant circuits that may be active simultaneously, precluding the synchronous activation of enough atrial myocardium to generate an identifiable p wave or coordinated atrial contraction. Either a sinus impulse or a stable atrial flutter reentrant circuit (flutter wave) may degenerate into the multiple reentrant circuits (multiple wavelets) characteristic of atrial fibrillation. [Cox et al., *J. Thoracic. Cardiovas. Surg.* 101:402–405 (1991)].

Degeneration of the stable activation patterns of sinus rhythm and atrial flutter into atrial fibrillation is enhanced when there is a disparity in the local refractory periods of closely approximated regions of atrial myocardium. However, atrial geometry, atrial anisotropy, and histopathologic changes in the atrial myocardium may also predispose to both atrial flutter and atrial fibrillation.

Atrial fibrillation currently afflicts over three million persons in the United States. [Cox et al., *J. Thoracic. Cardiovas. Surg.* 101:402–405 (1991)]. It is the most common sustained arrhythmia, increasing progressively in prevalence with advancing age, and occurring in 2%–4% of the population over the age of 60. Atrial fibrillation is associated with atherosclerosis, chronic rheumatic heart disease, and hypertensive heart disease. The medical treatment of atrial fibrillation is less than optimal in that it frequently fails to ablate the arrhythmia and is ultimately directed only toward the control of the ventricular response rate. This results in patients (1) continuing to experience the unpleasantness of an irregular heartbeat, (2) continuing to suffer the consequence of impaired hemodynamics because of loss of atrioventricular synchrony, and (3) remaining vulnerable to the thromboembolic complications of atrial fibrillation.

For example, certain antiarrhythmic drugs, like quinidine and procainamide, can reduce both the incidence and the duration of atrial fibrillation episodes. Yet, these drugs often fail to maintain sinus rhythm in the majority of patients. Atrio-venticular nodal blocking agent, e.g. drugs, like digitalis, Beta blockers, and calcium channel blockers, can also be given to control the ventricular response. However, many people are intolerant to such drugs. [Kerr, *PACE* 17:1203–1207 (1994)].

Nonpharmacologic tools to treat atrial fibrillation include atrial defibrillation, catheter ablation, and open heart surgery. While effective means of treatment, each possess unwanted drawbacks.

External electrical cardioversion/defibrillation has been an effective method for termination of atrial fibrillation. It has been a well-accepted mode of acute therapy for over thirty years. However, there is potential risk of myocardial damage, ventricular tachyarrhythmias, or thromboembolism with this technique. [Luderitz et al., *Am. J. Cardiol.* 77:45A–52A (1996)]. Most importantly, the procedure only terminates the event and does not treat the underlying problem.

Implantable atrial defibrillators have been used in patients recently. This method is accomplished by the implantation of an internal defibrillator and a nonthoractomy lead system. However, patients with frequent episodes of fibrillation or episodes of short duration and spontaneous termination are not good candidates and alternative methods of treatment must be attempted. Major problems involved with the implantation technique include the presence of continual pain, the risk of inducing ventricular tachycardia during low level shocks and rapid battery depletion. [Luderitz et al., *Am. J. Cardiol.* 77:45A–52A (1996)].

Ablation of the atrioventricular node (AV node) in patients with chronic or paroxysmal atrial fibrillation has been extensively described and provides relief in selected patients. The patient, however, is left in atrial fibrillation and therefore there is a persistent risk of thromboembolism and continued loss of contractile atrial function. This technique uses catheter ablation by radiofrequency energy to permanently disconnect the fibrillating atria from the ventricles. Pacing is then permanently provided to the ventricle. [Fritzpatrick et al., *Am. Heart J.* 131(3):499–507 (1996)]. In addition, radiofrequency catheter ablation has been used to create linear lesions in the right atrium. This technique uses a specially designed 14-polar catheter and results in the patient being free from arrhythmias or the need for medication for up to 3 months. Although encouraging results were obtained, the selection of patients that may utilize this specialized technique are very limited. Luderitz et al., *Am. J. Cardiol.* 77:45A–52A (1996)].

One open heart surgical procedure is the so-called "corridor" procedure. This approach separates the fibrillating atria from a strip of tissue connecting the sinus and the AV node. Because both right and left atria continue to fibrillate, the hemodynamic abnormalities associated with AF are not improved. In addition, the vulnerability to the development of left atrial thrombi is not alleviated. Originally, it was hypothesized that this small corridor of atrial tissue would not be large enough to sustain AF. However, AF may continue and anticoagulation remains necessary. [Luderitz et al., *Am. J. Cardiol.* 77:45A–52A (1996)].

Another open heart surgical procedure for treating atrial fibrillation, termed the "maze procedure", has been found to be effective in treating atrial fibrillation. The procedure makes a prescribed pattern of incisions to anatomically create a convoluted path, or maze, for electrical propagation within the left and right atria. The incisions direct the electrical impulse from the SA node along a specified route through both atria, resulting in a uniform contraction and therefore normal atrial transport function. The incisions finally direct the impulse to the AV node to activate the ventricles, restoring normal atrioventricular synchrony. The incisions are also carefully placed to interrupt the conduction routes of the common reentry circuits. Appropriately placed atrial incision not only (1) interrupt the conduction routes of the most common reentrant circuits, they also direct (2) the sinus impulse from the sinoatrial node to the AV node along a specified route and (3) preserve synchronous atrial electrical activation as a prerequisite for contraction. The maze procedure has been found effective in treating atrial fibrillation. Yet, despite its clinical success, the maze procedure is technically difficult to do and requires open heart surgery. Moreover, the procedure is not tailored to a specific patient and sometimes can result in a permanent loss of contractile atrial function. Because of these factors, only a few maze procedures are done each year. (U.S. Pat. No. 5,549,661 to Kordis et al., incorporated herein by reference).

What is needed presently is a safe method of treatment that is both cost effective and versatile enough to be used on a wide variety of cardiac diseases. The method would improve the patient's quality of life by allowing for increased performance of everyday tasks as well as providing a general satisfaction with overall health. In addition, it would lower the number of visits the cardiac patient must make to their physician, thus reducing health care costs. Also, the mortality rate for these patients will decline.

SUMMARY OF THE INVENTION

The present invention relates to new methods of treating cardiovascular disease, more particularly fibrillation of the heart. In one embodiment, the method comprises the steps of a) providing: i) a subject having a heart; ii) a means for sectioning the heart; and iii) a means for stimulating the heart; b) sectioning the heart into independent conduction zones with said sectioning means; and c) stimulating the independent conduction zones with said stimulating means.

In another embodiment, the method comprises the steps of a) providing: i) a subject having a heart, ii) a means for sectioning the heart, iii) a means for stimulating the heart, and iv) a catheter; b) introducing said catheter into said subject; c) introducing said sectioning means into said subject through said catheter; d) sectioning the heart into independent conduction zones with said sectioning means, and e) stimulating the independent conduction zones with said stimulating means.

It is not intended that the invention be limited to subjects with any one type of cardiac disease. Potential cardiac diseases include: atrial fibrillation (chronic or paroxymal), atrial flutter and ventricular fibrillation. Also, the age, sex, or degree of disease state is not intended to be in any way limiting to the present invention.

A preferred embodiment of the invention is sectioning of the heart by way of non-invasive means. However, it is contemplated that the creation of independent conduction zones by way of lesions may be accomplished with invasive as well as non-invasive surgical techniques.

In another embodiment, the heart has metal sutures placed in regions of the atria that need to be electrically isolated. This is performed during either a limited thoracotomy or during a median sternotomy that is being performed for another procedure (eg. coronary artery bypass graft, or valve replacement/repair). The ends of the suture are taken to the body surface, a technique that is similar to that used to take temporary epicardial pacing wires to the body surface. Once the patient has recuperated from the surgery, uncoupling is performed by passing either an electric current or other energy source such that uncoupling occurs at the metal suture-tissue interface. Once the uncoupling has taken place, the wires are removed by gentle traction (similar to the procedure used with the epicardial pacing wires).

In another embodiment, the heart is sectioned into independent conduction zones by way of catheter ablation. However, it is not intended that the invention be limited by any particular method of sectioning.

In a preferred embodiment, the catheter ablation forms curvilinear lesions onto the heart. It is not intended that the invention be limited by any particular number or configuration of lesions created by ablation. Also, the invention is not limited to the precise length, width, depth, or spacing between lesions.

While it is not intended that the present invention be limited by the particular method of catheter ablation, a preferred method is by radiofrequency. Other contemplated ablation or modification techniques include but are not limited to: electrical catheter, laser, ultrasound, cryogenics, surgery, and alcohol or phenol ablation.

In another embodiment, the heart is sectioned into at least two independent conduction zones. In addition, the sectioning of the heart into independent conduction zones is not intended to be limited to any particular chamber of the heart.

In a preferred embodiment, the means for stimulation is placed inside the body of the subject. However, it is contemplated that the means for stimulation may be externally placed as well (just under the skin or on the surface of the skin).

Where placed inside the body, the present invention contemplates an embodiment where the means for stimulation is attached to the surface of the heart (e.g. on the epicardial surface). However, it is also contemplated that the means for stimulation may lie in contact with the internal lining of the heart (e.g. on the endocardial surface).

In one embodiment, the means for stimulating the independent conduction zones are implantable solid state devices. In another embodiment, the means for stimulation is a pacemaker.

In another embodiment, the means for stimulating is comprised of at least one electrode and a power source. Further, it is not intended that the electrode(s) be limited in the number, size, or spacing, the configuration and shape being variable.

The means for stimulating the independent conduction zones is contemplated to be used on any chamber of the heart and should not be thought to be limited to either the left or right, or atrium or ventricle, or any combination thereof. The stimulation is not intended to be limited by its intensity, the intensity being adjusted by increasing the number of pulses, the width of the pulses, the amplitude of the and/or their frequency. Moreover, they may be individual or train pulses.

In another embodiment, the means for stimulation is able to automatically vary the stimulation depending on physiologic conditions. These conditions being a change in physical activity, mixed venous oxygen saturation, right ventricular pressure, or any other conditions contemplated by one skilled in the art.

Definitions

The following definitions are to be used to further explain the invention and should in no way be used to limit the scope of the invention.

"Subject" as used herein refers to a vertebrate. Preferably, the vertebrate is a human.

"Independent conduction zones" as used herein are electrically isolated regions created by the making of lesions within the chamber(s) of the heart.

"Catheter" as used herein refers to a device for insertion into canals, vessels, passageway or body cavities to permit recording of electrograms and in a preferred embodiment, a catheter can be used in a catheter ablation technique. "Catheter ablation" is a technique wherein lesions are created in the heart muscle tissue by insertion of a catheter followed by either radiofrequency, thermal, or cavitational ablation.

"Means of sectioning" as used herein refers to a means for physically terminating the electrical communication between cells. In one embodiment heart tissue is ablated by way of a medical device. In a preferred embodiment, the medical device is a catheter which emits radiofrequency energy.

"Means for stimulating" as used herein refers to a medical device which produces a burst of energy either in individual or pulse trains in a predetermined or varied amount. In a preferred embodiment, a signal from a sensing system applies pacing to the independent conduction zones.

"Solid state electrical device" as used herein refers to devices which utilize either electrical, magnetic, or photic properties of solid materials.

"Non-invasive" as used herein refers to the ability to enter the subjects body without cutting into the tissues of the body. In a preferred embodiment, the non-invasive means is through a blood vessel.

"Curvilinear lesions" as used herein refers to lines of section on the inside of the heart (i.e., endocardium) such that communication from one side of the line to the other is not possible.

"Cardiac disease" as used herein refers to a state in which the heart of a subject is no longer able to function within normal parameters.

"Internally" as used herein refers to the state of being inside the body.

"Automatically varies the amount of stimulation depending on physiologic conditions" as used herein refers to the pacing device changing the phase of stimulation of the various independent conduction zones such that the maximal cardiac output is achieved.

"Radiofrequency energy" as used herein refers to an electromagnetic wave frequency intermediate between audio frequencies and infrared frequencies.

"Re-establishing functional communication" as used herein refers to the pacing of independent conduction zones in a way such that there is a coordinated contraction of both the right and left atria. Conduction therefore starts away from the AV groove and proceeds towards this region, therefore ejecting blood into the ventricle.

"Temporal protocol" as used herein refers to the time sequence for pacing independent conduction zones.

DESCRIPTION OF THE INVENTION

Figure 1A:
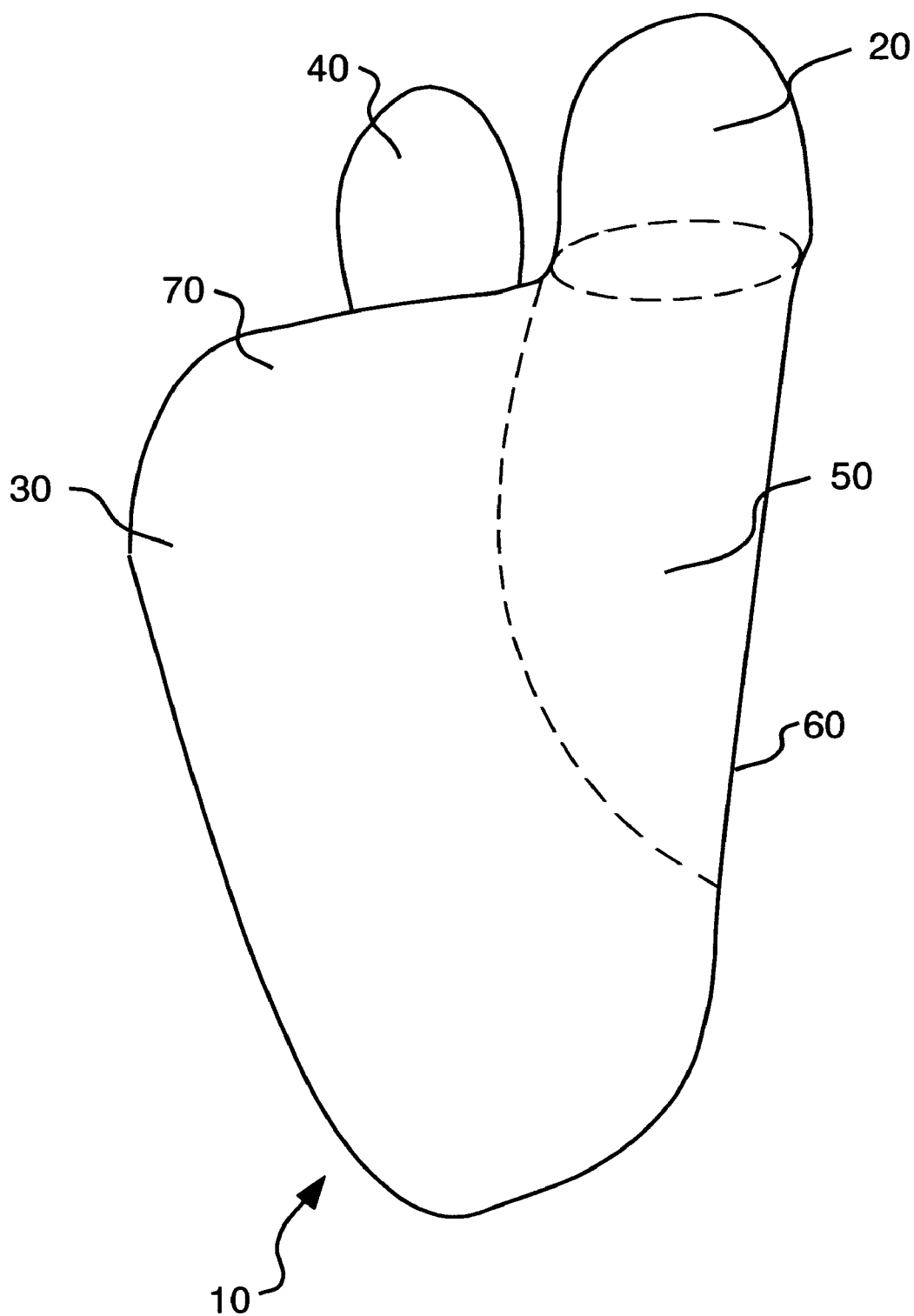
FIG. 1A is a diagram depicting the electrically isolated atrial sections of one preferred embodiment.

The present invention provides devices and methods for control of heart fibrillation. In a preferred embodiment the present invention is used to control atrial fibrillation. One proposed embodiment of the invention contemplates the use of non-invasive procedures for both ablation and implantation of a pacing device which would also eliminate the morbidity and mortality associated with open-heart surgical techniques. The present method of treatment is a substantial improvement over existing techniques because it presents a potential "cure" for atrial fibrillation, and does not require defibrillation. In one preferred embodiment, a subject with a diseased heart is treated by sectioning the heart into independent conduction zones by catheter ablation, followed by stimulating the independent conduction zones with a heart pacing device.

Subjects of which the present method of treatment is proposed to cure include those with the following known cardiac diseases: atrial fibrillation, ventricular fibrillation, ventricular tachycardia and complete or partial atrioventricular block. However, it is not intended that the present method be limited to only the above proposed cardiac diseases. It is also not intended that the invention be limited as to a particular subject. A subject as described in the definition section refers to a vertebrate, preferably a human.

I. Heart Function

The operation of the heart is regulated by electrical signals produced by the heart's sino-atrial (SA) node. Each signal produced by the SA node spreads across the atria and ventricles of the heart, depolarizing the muscle fibers as it spreads. Atrial and ventricular contractions occur as the signal passes. After contracting, the myocardial cells repolarize during a short period of time, returning to their resting state. Once repolarized, the muscle cells are ready to be depolarized again by a signal from the SA node.

At rest, the normal adult SA node produces a signal approximately 60 to 85 times a minute, causing the heart muscle to contract, and thereby pumping blood to the remainder of the body. This constitutes the repetitive, cyclic behavior of the heart. Each cycle in the operation of the heart is called a cardiac cycle.

Atrial geometry, atrial anisotropy, and histopathologic changes in the left or right atria can, alone or together, form anatomical obstacles. The obstacles can disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Abnormal, irregular heart rhythm called arrhythmia, results. This form of arrhythmia is called atrial fibrillation, which is a very prevalent form of arrhythmia.

To analyze the heart's operation, a variety of techniques have been developed for collecting and interpreting data concerning the electrical activity of the heart. One of the most basic of these approaches is the electrocardiograph (ECG). As an electrical signal spreads across the heart, which we shall call an electrical wave front, an ECG repetitively measures the voltages at various electrodes relative to a designated "ground" electrode. The ECG typically plots each lead over an interval of time such that the heart's electrical activity for one or more cardiac cycles is displayed for purposes of monitoring or analysis. The three most common ECG's are known as the "12 lead", the "18 lead," and the vector cardiograph.

A cardiac cycle as measured by the ECG is partitioned into three main elements which reflect the electrical and mechanical operation of the heart. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." The portion of a cardiac cycle representing repolarization of the ventricular muscle fibers is known as a "T-wave." It is through the use of an ECG that one is able to determine whether fibrillation is or is not occurring and allows one to manipulate the heart tissue to provide treatment.

II. Independent Conduction Zones

One embodiment of the invention provides a method of treatment wherein the atrium or ventricle is sectioned into distinct independent conduction zones (ICZ) electrically isolated from each other. In one embodiment, the ICZs are created by non-invasive interventions such as radiofrequency, thermal or cavitational ablation. In an alternative embodiment, it is contemplated that localized drug or gene delivery may be used to anatomically or functionally uncouple the electrical connection between the cells.

One aspect of the invention provides a method of ablating tissue in the heart to treat atrial fibrillation by introducing into a selected atrium a sectioning means, such as an elongated energy emitting element that can be flexed along its length from a generally straight shape into a variety of curvilinear shapes. The proposed method exposes the catheter into a desired shape. The method applies ablating energy to or through the catheter to destroy tissue, forming an elongated lesion having a contour that follows the flexure of the catheter. The method is then repeated with tissue exposure, catheter flexing and energy application steps being provided at different spaced regions along the atrial wall. In this way, a convoluted lesion pattern comprising elongated straight lesions and elongated curvilinear lesions is produced. This electrical uncoupling interrupts the reentry circuits thereby preventing atrial fibrillation In a preferred embodiment, the method introduces the catheter through a vascular approach, without opening the heart. In this embodiment, the method applies radiofrequency electromagnetic energy to ablate the tissue. The working catheter segments contemplated are typically about 6 French to 8 French in diameter and with a sheath member approximately 7–10 French in diameter.

In one proposed embodiment, functional communication between the cells would be reestablished through the use of implantable solid state devices (ISSD) in each ICZ, which communicate with each other in a controlled way so as to establish a temporal protocol for stimulating each ICZ.

In a preferred embodiment, these ISSDs would be implanted using noninvasive, catheter-based techniques. In one embodiment, the ISSDs will utilize microcircuit technology to incorporate a sensing element, a pacing element, a computing element and a power element.

This procedure will essentially establish a distributed pacing system either under control of a master pacing device implanted under the skin, or under natural cardiac control (sino-atrial or atrio-ventricular node) with appropriate sensors in the ISSDs. Communication within the ICZs will be by normal cell-to-cell coupling and between the ICZs by the ISSDs.

III. Pacemakers

A pacemaker maintains the heart rate of a patient between a certain programmable range. For example, in humans that range is typically between 60–80 beats per minute (lower rate) and 120–160 beats per minute (upper rate). As noted above, in one embodiment, the present invention contemplates a pacemaker as a means for stimulating the independent conduction zones and reestablishing functional communication between the zones. A pacemaker automatically applies a pacing impulse to the heart of sufficient magnitude to depolarize the tissue. The device is adapted to continue delivering intermittent pacing to the heart in the event that the heart fails to return to its normal behavioral pattern, and has the ability of automatically regaining sensing control over a functional heart, thereby insuring that further pacing is inhibited.

The pacemaker circuit comprises two basic subsystems; a sensing system, which continuously monitors heart activity; and a stimulation system which upon receiving a signal from the sensing system applies a pacing impulse to the myocardium through an intravascular electrical lead. A first bipolar lead is coupled to the pulse generator and has an electrode located at its distal end to sense and pace the atrium. A second bipolar lead coupled to the generator is used for sensing and pacing the ventricle. A circuit is provided for applying impedance measuring current pulses between one of these electrodes and the other.

In one embodiment, an off the shelf pacemaker capable of both atrial and ventricular pacing/sensing is used. The specific pacemakers preferred for this purpose include a Medtronic Thera, a Medtronic Elite 2 (both made by Medtronic, Inc. Minneapolis, Minn.), or Pacesetter Trilogy DR+(Pacesetter, a St. Jude's company, Minneapolis, Minn.) as these have a minimum programmable delay between atrial and ventricular pacing of 40 msec. To effectuate pacing according to one embodiment of the invention, both the leads from the atrial and the ventricular segment of the pacemaker are connected to the atrium. To allow more than one segment to be paced per lead, a bifurcation system can be used. Such leads are commercially available and can be used as an off the shelf product. The Y-adapter (for example CPI MODEL #6835, or #6024, made by Cardiac Pacemakers Inc., Minneapolis, Minn.) would allow one of the sockets from the pacemaker (atrial or ventricular) to then be bifurcated to two leads. Therefore, each output would then be able to pace two electrically isolated segments of the atrium. For epicardial pacing, CPI model #4312 lead (Cardiac Pacemakers Inc., Minneapolis, Minn.) can be used and this has a 4.75 mm pin. For endocardial pacing, CPI model #4161 (Cardiac Pacemakers Inc., Minneapolis, Minn.) could be used. In this manner, a standard dual chamber pacemaker could be used to pace four ICZ's.

A. Sensing Elements Of A Pacemaker

In a standard dual chambered pacemaker, the sensing circuits monitor activity both in the atrium and ventricle. If a sensed event occurs in the atrium, this initiates a ventricular paced event if no ventricular activity occurs during the programmed atrioventricular delay. If no sensing occurs in the atrium or ventricle, pacing is initiated to maintain the programmed lower rate.

When the pacemaker device is used for the present invention, similar sensing algorithms will be useful in the appropriate pacing of the various ICZs. It is particularly desirable that the pacemaker include a sensor of a physiologic parameter related to demand for cardiac output, such as an activity sensor, a respiration sensor or an oxygen saturation sensor. Various dual chamber pacing devices have incorporated some form of sensor to provide a physiologic pacing rate. Similar sensing is contemplated for the present invention to maintain a physiologic rate.

B. Pacing Elements

In a standard dual chamber pacemaker, pacing of both atrium and ventricle is possible. In the current invention, pacing of the various elements will take place once requested by the sensing algorithm. The standard burst generator pacemaker employs appropriate technology for the generation of stimulation pulses in the form of individual pulses or pulse trains having an amplitude up to 7 V and a pulse width of up to 1 msec. Most pacemakers have these parameters as a programmable option. The pacing rate is also programmable in most pacemakers and the range is between 35–160 beats/min.

Given that the circuitry for pulse generation has become well known to those skilled in the art, no detailed disclosure is included herein. Specific timing, amplitude, duration and the number of pulses is controlled by a microprocessor via data bus under the control of a program stored in memory.

C. Computing Elements And Software

The computing element is a microprocessor which operates as an interrupt driven device, and is awakened by interrupts from pacer timing/control circuitry corresponding to the occurrence of sensed R-waves and corresponding to the generation of cardiac pacing pulses. These interrupts are provided via data/address bus. Any necessary mathematical calculations will be performed by the microprocessor and any updating of the values or intervals controlled by pacer timing/control circuitry take place following such interrupts.

D. Power Elements

Any form of implantable stimulating device must be powered by a portable, depletable power source, such as a battery. When the battery is depleted of its energy, it is necessary to explant the device and implant a replacement. As a result, for an implantable device to be considered commercially viable, it is generally believed that the device should have a predicted lifetime of a number of years, such as five years, which is contemplated for the proposed device.

While the stimulating device is described in the form of a microprocessor based programmable stimulator, the method of treatment incorporating the device is sufficiently simple that the stimulating device could readily be embodied in the form of a full custom digital integrated circuit based device or even a device employing analog timing units. Therefore, the above disclosure should be considered explanatory, rather than limiting with regard to what is claimed.

Experimental

The following example serves to illustrate certain preferred embodiments and aspects of the present invention and is not to be construed as limiting the scope thereof.

In the experimental disclosure which follows, the following abbreviations apply: kHZ (kilo-hertz); SA (sinoatrial); AV (atrioventricular); msec (millisecond); QRS ("Q", "R", and "S" points of a cardiac cycle); and ECG (electrocardiogram).

EXAMPLE 1

Using an open chest canine preparation, a portion of the atrium was sectioned into three electrically isolated regions as depicted in FIG. 1A. Linear lesions were produced using a radionics 300 kHz, approximately 40–50 watt radiofrequency generator [Radionics Inc., Burlington, Mass.] in two dogs. In a third dog, the lesions were made by cutting the atrium with a scalpel after clamping the relevant portion of the tissue to control bleeding.

Figure 2:
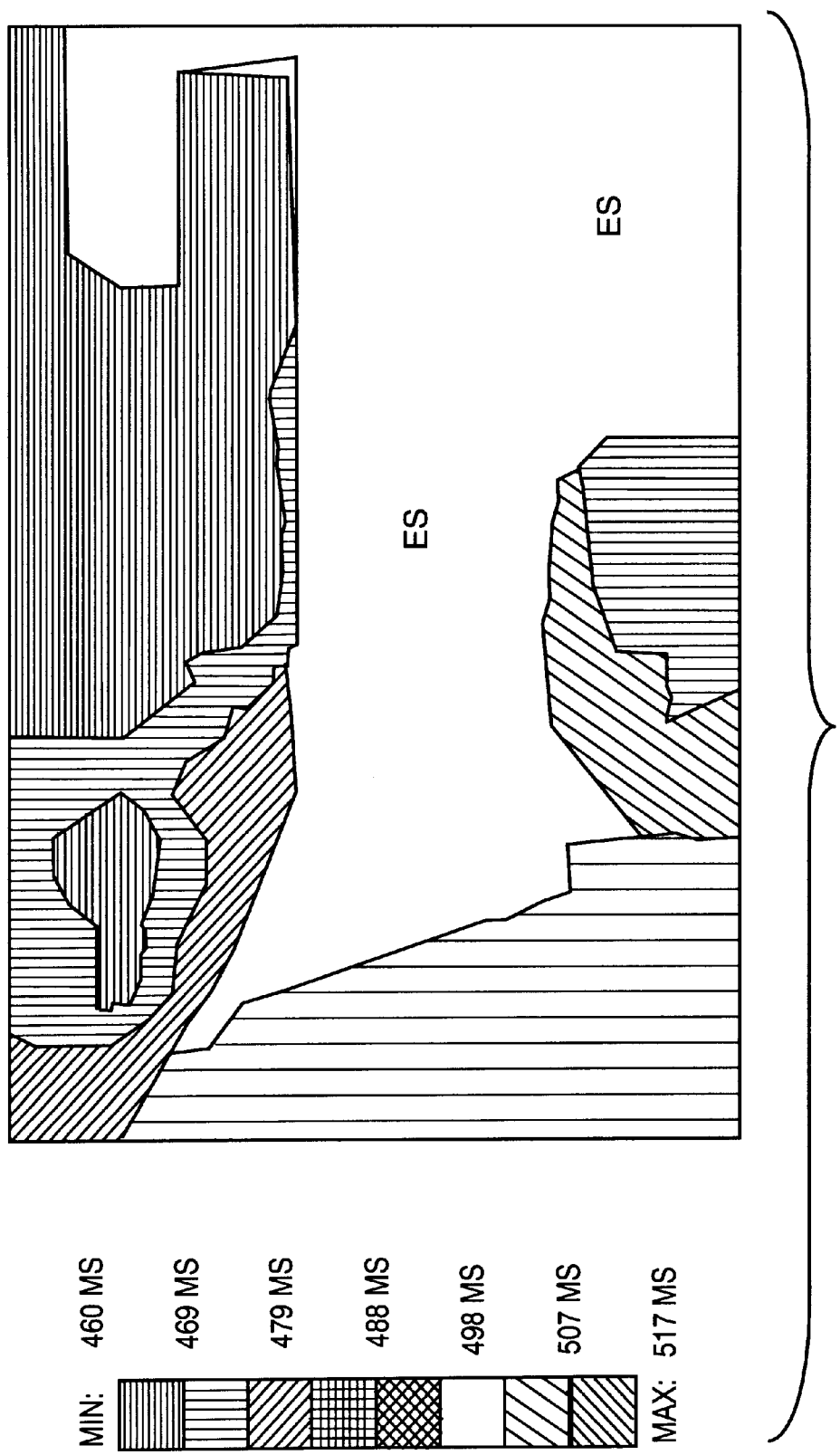
FIG. 2 is an isochronal map of the atrium after sectioning which is representative of one embodiment of the present invention.
Figure 3:
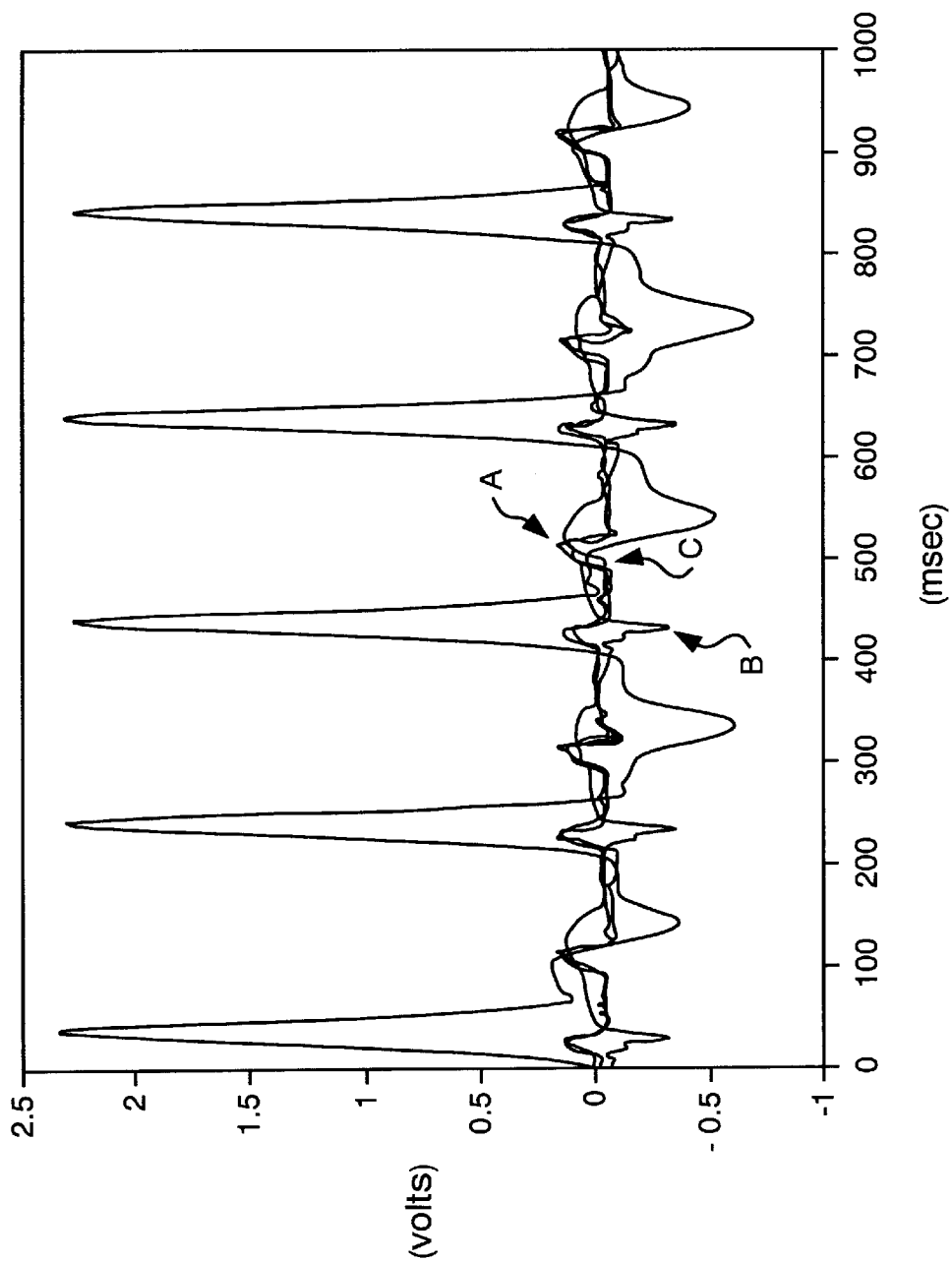
FIG. 3 depicts an electrogram during pacing in the atrium proper.
Figure 4:
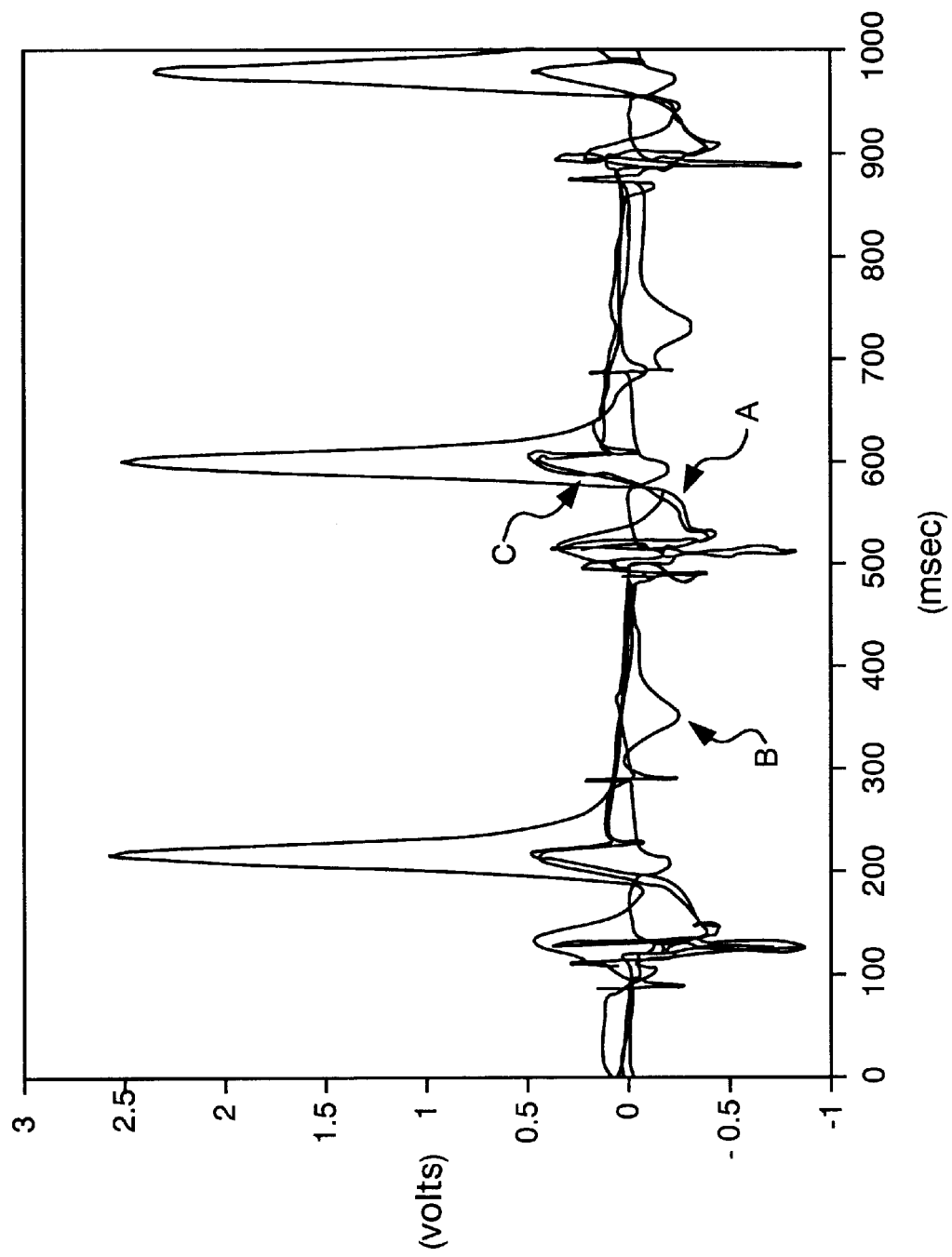
FIG. 4 depicts an electrogram from the "atrium proper" where the ventricles were not captured by the pacing.

Electrical isolation of the segments was documented both by high density electrode mapping using the CardioMAP equipment [Prucka Engineering, Houston, Tex.] as depicted in FIG. 2 and also by pacing maneuvers. FIG. 2 displays an isochronal map of the atrium during sinus rhythm, after the sectioning procedures were preformed. FIGS. 3 and 4 are examples demonstrating electrical uncoupling with pacing. FIG. 1A depicts the isolation of the right atrial appendage and the medial segment of the atrium with similar mapping and pacing techniques.

A system for establishing normal atrial activity after sectioning was developed on a personal computer (PC) equipped with two digital analog boards. These two boards had two A-D (digital to analog) outputs each. (DT3001 and DT2821, Data Translations, Inc.) The Hewlett Packard HPVEE was used to pace the isolated segments of atria in addition to the right and left atrium. Coordinated contractile atrial function was documented visually and by measuring the pressure in the right atrium using a Swan Ganz catheter [Abbott Critical Care Systems, North Chicago, Ill.].

The experiments demonstrate complete electrical isolation of a segment of atria. In addition, they show that both electrical and contractile atrial function can be achieved through the use of an external PC driven software program.

FIG. 1A illustrates the ablated sections of the atrium (10). The sections include: the right atrial appendage (20), atria proper (30), which is the area including the SA node (70), the AV node (30); the left atrial appendage (40), the medial section (50), which is the central region of the right atrium, and AV groove (60).

FIG. 2 displays a isochronal map of the atrium following sectioning of the tissue. The upper left portion of the map shows the earliest activation and corresponds to the SA node activity. The center and lower right regions correspond to the medial section which is electrically silent ("ES") since it is isolated from the SA node. The activation can be seen spreading around the region of isolation in a counter clockwise direction, to the region on the bottom center which corresponds roughly to the AV node.

FIG. 3 illustrates an electrogram during pacing in the "atrium proper". Line A is the limb lead, Line B is an electrogram from the medial segment of the sectioned atrium, and Line C is from a distal portion of the atrium proper. During pacing the "atrium proper" at a cycle length of 200 msec., there is a normal conduction to the ventricle as the QRS complexes on the surface EKG occur every 200 msec. No electrical activity is noted from the medial segment of the sectioned atria, however, far-field ventricular activity is noted. The electrograms from the distal portion of the atria proper show local activation occurring approximately 80 msec after pacing. This 80 msec is the conduction time from the pacing site to the recording site.

FIG. 4 illustrates an electrogram during pacing in the atrium proper as described above, however, the ventricles were not captured by the pacing and were being paced by the SA node at a cycle length of approximately 380 msec. Local atrial activity is noted following the pacing stimulus only in the medial segment of the atrium (Lines A, B and C are as described for FIG. 3, above).

Figure 5:
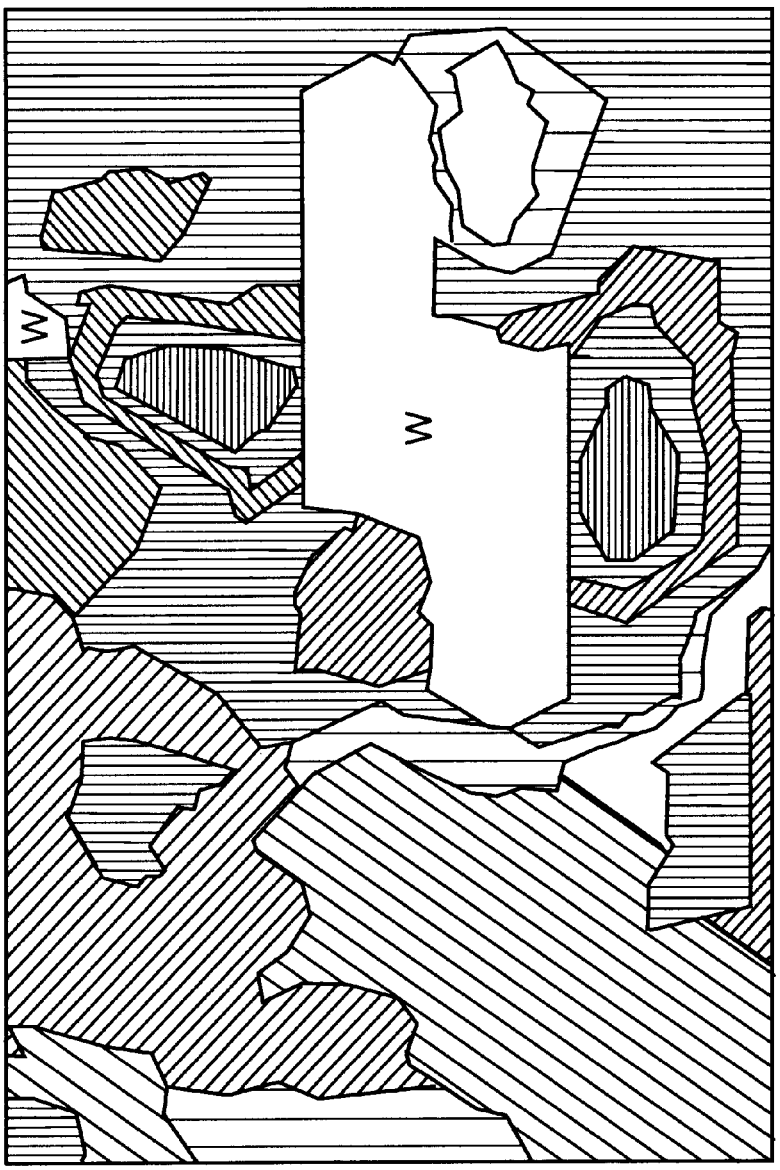
FIG. 5 is an isochronal map of the atrium following electrical recoupling of two sectioned portions of the atria which is representative of one embodiment of the present invention.
Figure 5:
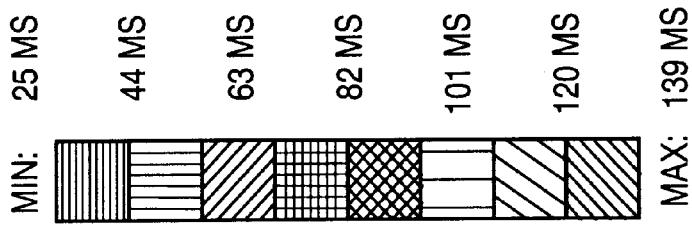

FIG. 5 illustrates an isochronal map following recoupling of two isolated portions of the atria. The white portions (W) denoted on the map represent areas that are not electrically active. It should be noted that the mapping array is not of an identical position to before the ablation procedure as depicted in FIG. 2.

EXAMPLE 2

Once the atrium has been sectioned into electrically isolated regions this results in the termination of atrial fibrillation. This has been demonstrated in previous studies for example the maze procedure by Cox. The next step comprises the attachment of either a solid state device or a pacing lead to the center of these isolated segments. Another possibility would be to first place these leads or solid state devices at regions of the heart that require pacing and then perform sectioning to isolate these regions from each other.

An advantage of this is that, once the sectioning has been performed, one is able to demonstrate electrical isolation as seen in the example above. A locator signal (either radiofrequency on ultrasound) can be emitted from the tip of the lead or the solid state device and this helps in the three dimensional localization of the solid state device as the lesions are made.

Figure 1C:
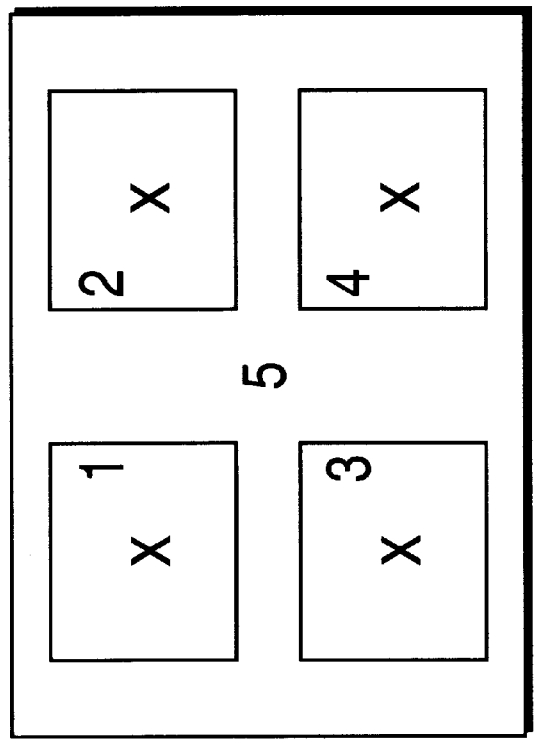
FIGS. 1B and 1C display two possible ways of sectioning the atrium.
Figure 1B:
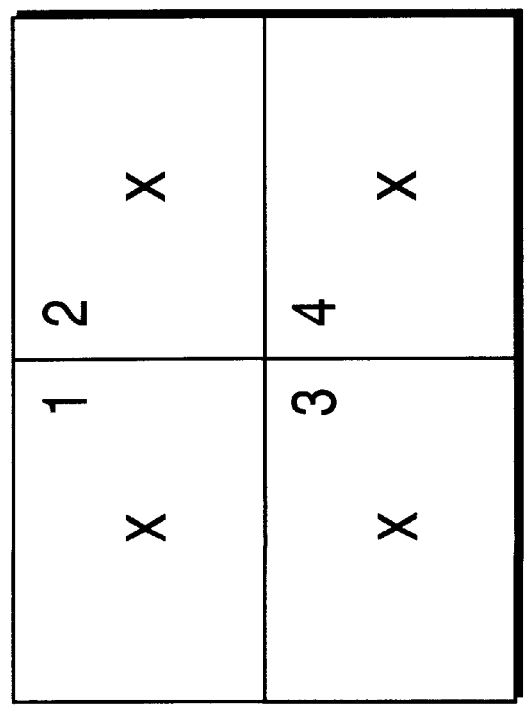

The exact shape and location of the electric isolated segments can be patient specific. What is required to terminate a fibrillation is to reduce the surface area of the connected portions of the atrium. The electrically isolated segments need not be connected to one another for this invention. FIG. 1B and 1C displays two possible ways of sectioning the atrium (where "X" represents the pacing device and the independent conduction zones are shown as 1–5).

Figure 6:
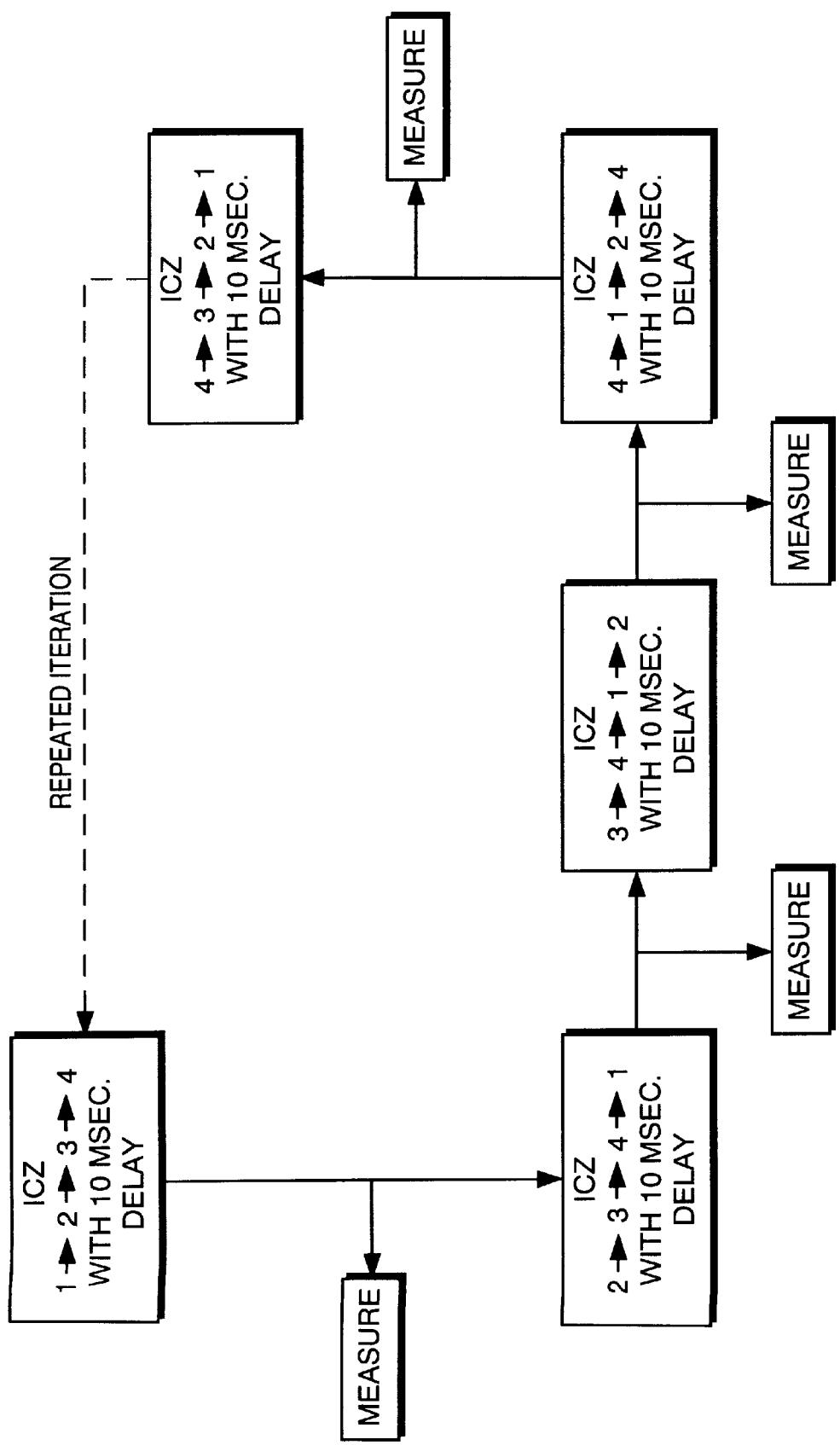
FIG. 6 is a flow chart of software that controls the pacing technique of one embodiment of the present invention.

The pacing leads can then be connected to the pacing device to establish communication between themselves and the control device such that pacing of the various sections is then possible. The exact timing of the independent conduction zones can be optimized for the specific patient using the Swan Ganz recording in the right atrium and also the pulmonary capillary wedge pressure recording (a marker of left atrial pressure). The flow chart (FIG. 6) describes the schematic view that will be used to optimize the timing of pacing of the independent conduction zones.

In this example, four independent conduction zones (ICZ's) are assumed. Pacing of the ICZ's is performed in sequence starting off with pacing one followed by two, three, and then four with a 10 msec. delay between each pacing site. Different sequence of pacing is performed and with each sequence, measurements of mean pulmonary wedge pressure and mean right atrial pressures are taken.

The ICZ sequence that results in the largest mean RA and mean pulmonary capillary wedge pressure is chosen for that particular patient. This pacing sequence is then used as the optimal pacing sequence.

The algorithm need not go through every iteration as pacing the higher segments first would be more beneficial, therefore this will limit the number of iterations required for the measurement.

EXAMPLE 3

This example describes an alternative pacing method. In this embodiment, the exact timing of the independent conduction zones can be optimized for the specific patient using the measurement of the P wave duration and amplitude. This technique has an advantage over the Swan-Ganz technique in that it is non-invasive and can be performed during a clinic evaluation.

The flow chart of FIG. 6 is again applicable. The timing of pacing of the independent conduction zones is optimized by achieving the narrowest P wave duration and greatest P wave amplitude. Again, pacing of the ICZ's is performed in sequence starting off with pacing one followed by two, three, and then four with a 10 msec. delay between each pacing site. A different sequence of pacing is performed and with each sequence, a measurement of the P wave duration is taken.

Figure 7:
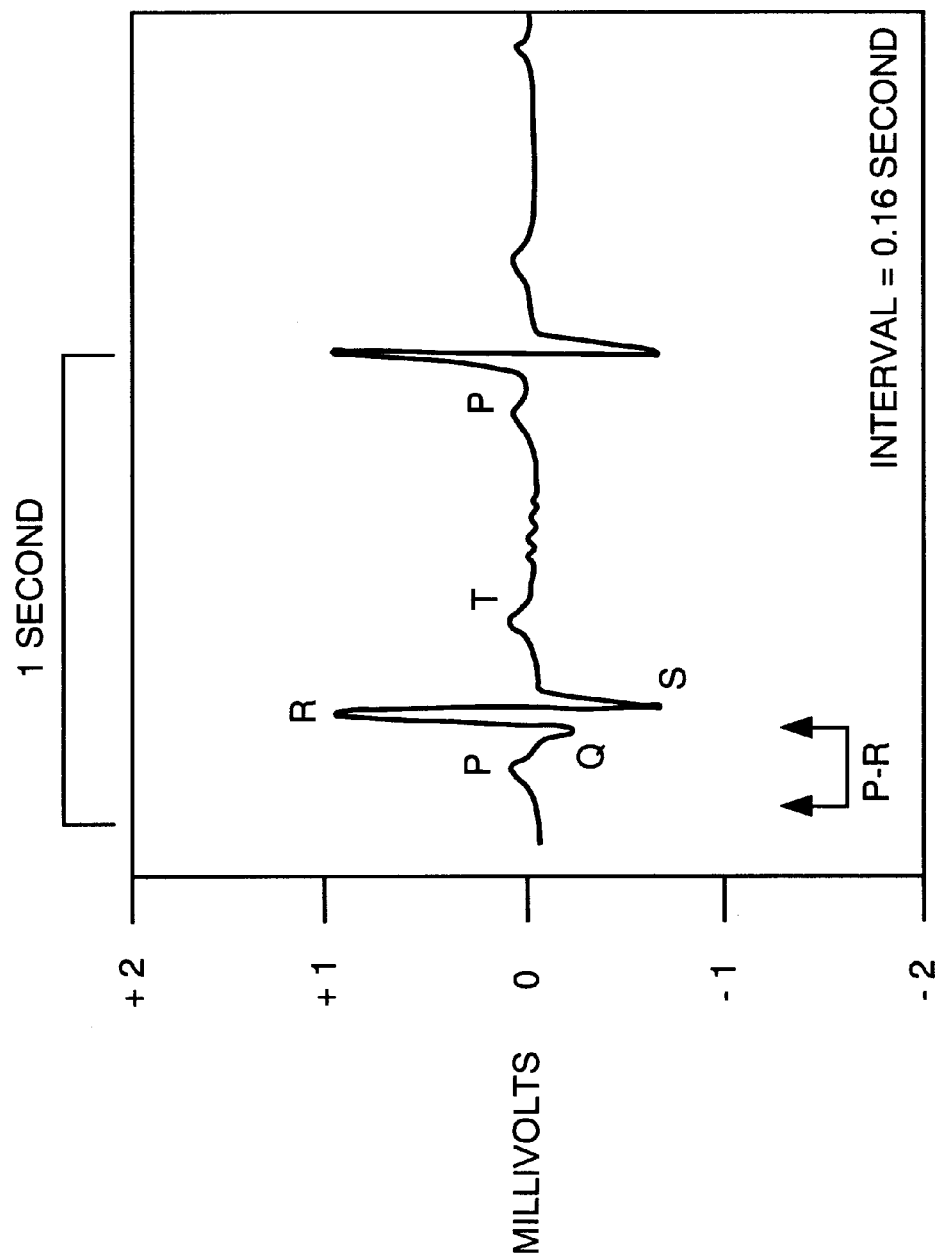
FIG. 7 is a normal electrocardiogram.

FIG. 7 shows a normal electrocardiogram (provided herein as a reference). The first deflection, P, is due to excitation of the atria. The QRS deflections are due to excitation (depolarization) of the ventricles. The measurements can be either on signal average of 20 to 200 PQRS complexes or can be on an individual beat by beat basis. The advantage of signal averaging is that the signal to noise ratio is increased and therefore makes the measurement more accurate.

The ICZ sequence that results in the narrowest (i.e. shortest) P wave duration and the greatest P wave amplitude is chosen for that particular patient. This pacing sequence is then used as the optimal pacing sequence.

The algorithm need not go through every iteration as pacing the higher segments first would be more beneficial, therefore this will limit the number of iterations required for the measurement.

From the above it is clear that the present invention provides a method of treating irregular atrial or ventricular activity that is both cost effective and versatile. The method will improve the patient's quality of life by allowing for increased performance of everyday tasks as well as providing a general satisfaction with overall health. The method of treatment will also lower the number of visits the cardiac patient must make to their health care provider which in turn will reduce their overall health care costs. Any further improvements and modifications which become apparent to persons of ordinary skill in the art only after reading this disclosure, the drawings and the following claims are deemed within the spirit and scope of the present invention.

We claim:

1. A method, comprising the steps of:
  a) providing:
    i) a subject whose heart has been sectioned into independent conduction zones, thereby defining a plurality of isolated segments,
    ii) a means for stimulating said heart, said means comprising a plurality of pacing leads; and
    iii) a P wave measuring means;
  b) attaching a pacing lead to each of said isolated segments;
  c) stimulating said independent conduction zones with said stimulating means, said stimulating comprising stimulating each of said independent conduction zones in series to define a phase of stimulation; and
  d) measuring, with said P wave measuring means, the P wave generated by said stimulating of step c);
  e) changing said phase of stimulation of said independent conduction zones; and
  f) repeating steps c), d) and e) until the narrowest P wave duration and the greatest P wave amplitude is measured, thereby providing coordinated contraction of both the right and left atria of said heart of said subject.

2. The method of claim 1, wherein said heart is sectioned into at least four independent conduction zones.

3. The method of claim 1, wherein said means for stimulating said heart comprises at least one electrode and a power source.

4. The method of claim 1, wherein said means for stimulating are solid state electrical devices.

5. The method of claim 1, wherein said means for stimulating is a pacemaker.

6. A method, comprising the steps of:
  a) providing:
    i) a means for stimulating said heart, said means comprising a plurality of pacing leads;
    ii) a subject whose heart has been sectioned into independent conduction zones, thereby defining a plurality of isolated segments, each of said segments attached to said stimulating means via said pacing leads; and iii) a P wave measuring means;

b) stimulating said independent conduction zones with said stimulating means, said stimulating comprising stimulating each of said independent conduction zones in series to define a phase of stimulation; and c) measuring, with said P wave measuring means, the P wave generated by said stimulating of step b);

d) changing said phase of stimulation of said independent conduction zones; and e) repeating steps b), c), and d) until the narrowest P wave duration and the greatest P wave amplitude is measured, thereby providing coordinated contraction of both the right and left atria of said heart of said subject.

7. The method of claim 6, wherein said heart is sectioned into at least four independent conduction zones.

8. The method of claim 6, wherein said means for stimulating said heart comprises at least one electrode and a power source.

9. The method of claim 6, wherein said means for stimulating are solid state electrical devices.

10. The method of claim 6, wherein said means for stimulating is a pacemaker.

11. A method, comprising the steps of:

a) providing:
   i) a means for stimulating said heart, said means comprising a plurality of pacing leads;
   ii) a subject whose heart has been sectioned into independent conduction zones, thereby defining a plurality of isolated segments, each of said segments attached to said stimulating means via said pacing leads; and
   iii) a pressure measuring means;

b) stimulating said independent conduction zones with said stimulating means, said stimulating comprising stimulating each of said independent conduction zones in series to define a phase of stimulation; and c) measuring, with said pressure measuring means, the mean pulmonary wedge pressure and mean right atrial pressure of said heart of said subject generated by said stimulating of step b);

d) changing said phase of stimulation of said independent conduction zones; and e) repeating steps b), c), and d) until the largest mean right atrial and mean pulmonary capillary wedge pressure is measured, thereby providing coordinated contraction of both the right and left atria of said heart of said subject.

12. The method of claim 11, wherein said heart is sectioned into at least four independent conduction zones.

13. The method of claim 11, wherein said means for stimulating said heart comprises at least one electrode and a power source.

14. The method of claim 11, wherein said means for stimulating are solid state electrical devices.

15. The method of claim 11, wherein said means for stimulating is a pacemaker.

* * * * *